United States Patent [19]

Kaufhold

[11] 4,433,175
[45] Feb. 21, 1984

[54] PROCESS FOR THE PRODUCTION OF PURE NEOHEXANOL

[75] Inventor: Manfred Kaufhold, Marl, Fed. Rep. of Germany

[73] Assignee: Chemische Werke Huels, A.G., Marl, Fed. Rep. of Germany

[21] Appl. No.: 444,265

[22] Filed: Nov. 24, 1982

[30] Foreign Application Priority Data

Nov. 24, 1981 [DE] Fed. Rep. of Germany ....... 3146493

[51] Int. Cl.$^3$ .................. C07C 29/136; C07C 31/125; C07C 44/29
[52] U.S. Cl. .................................... 568/471; 560/248; 562/606; 568/885
[58] Field of Search ................. 568/885, 471; 560/248

[56] References Cited

U.S. PATENT DOCUMENTS

| | | | |
|---|---|---|---|
| 2,091,800 | 8/1937 | Adkins et al. | 568/885 |
| 2,123,520 | 7/1938 | Babcock et al. | 568/471 |
| 2,986,577 | 5/1961 | Kurhajec | 568/885 |
| 3,173,959 | 3/1965 | Rittmeister | 568/885 |
| 3,180,898 | 4/1965 | Eesenlohr et al. | 568/885 |

OTHER PUBLICATIONS

Sarel et al., "J. Am. Chem. Soc.", vol. 78, (1956), pp. 5416–5419.

Ipstieff et al., "J. Am. Chem. Soc.", vol. 73, (1951), pp. 553–555.

*Primary Examiner*—J. E. Evans
*Attorney, Agent, or Firm*—Millen & White

[57] ABSTRACT

For the production of neohexanol with a purity above 99%, a chlorine content of less than 10 ppm, and a sulfur content of less than 5 ppm, 3,3-dimethylbutyric acid with a chlorine content below 650 ppm, preferably below 100 ppm, is first esterified, optionally after distillatory separation into a portion richer in chlorine with a chlorine content above 650 ppm, preferably above 100 ppm, and into a portion low in chlorine with a chlorine content below 650 ppm, preferably below 100, with an alcohol boiling above 117° C., preferably an octyl alcohol. The resultant ester is separated by distillation into fractions richer in chlorine with chlorine contents above 10 ppm and into fractions low in chlorine with chlorine contents below 10 ppm. The ester of low chlorine contents below 10 ppm is hydrogenated to neohexanol over a barium-activated copper chromite catalyst under a pressure of 200–300 bar, at 120°–22° C., and with catalyst loads of 0.05–1.0 liter of hydrogenation feed/liter of catalyst . hour. The high purity of the neohexanol permits catalytic dehydrogenation to neohexanal.

14 Claims, No Drawings

PROCESS FOR THE PRODUCTION OF PURE NEOHEXANOL

BACKGROUND OF THE INVENTION

The present invention relates to a process for the production of pure neohexanol having a purity, for example determined by gas chromatography, of above 99.0% and with chlorine and sulfur contents of less than 10 and 5 ppm, respectively. The process involves esterification of a dimethylbutyric acid low in chlorine with an alcohol boiling above 117° C.; purification of the ester by distillation; and subsequent catalytic hydrogenation to the alcohol.

Syntheses of neohexanol are described in the literature, such as, for example, in U.S. Pat. Nos. 2,481,157 and 2,481,158. These propose a reaction of vinyl chloride with tert-butyl chloride in a pressurized reactor. In this process, a chlorine compound is obtained as an intermediate product in moderate yield. Hydrolysis of the intermediate product under pressure produces neohexanal. One disadvantage in this process is the high technical expenditure, the low yield, and the inadequate purity of the aldehyde. The high chlorine content of far above 10 ppm causes especially great problems during the further processing of the aldehyde. For example, the aldehyde cannot be reduced to neohexanol by catalytic hydrogenation due to corrosion and catalyst poisoning derived from the chlorine content.

In a two-stage process for the production of neohexanol (German Patent 925,229 = British Pat. No. 693,390), ethylene and isobutene are reacted with 95.5% strength sulfuric acid at −15° C. and under about 10 bar. The resultant sulfuric acid esters are hydrolyzed to the alcohol in a second stage. This method is technically expensive due to the required pressure, the low temperatures, and the corrosive medium, and results in relatively low yields of at most 60 polar percent.

Ipatieff et al (Journal of American Chemical Society 73: 553 [1951]) suggests a synthesis of neohexanol from 1-chloro-3,3-dimethylbutane by heating with aqueous potassium carbonate solution to 230° C. In this process also, the yield is low, i.e. 65%, and the technical expenditure is very high due to the corrosive medium and the high temperatures. Furthermore, the chlorine compound employed is hard to manufacture industrially because its synthesis, by the so-called Schmerling method (Journal of American Chemical Society 67: 1152 [1945]), requires low temperatures, for example of −60° or −40° C.

In contrast, a process wherein 3,3-dimethylbutyric acid is reduced with lithium aluminum hydride in ether provides a yield of 83.5% (Sarel, Newmann, Journal of American Chemical Society 78: 5416, 5417, 5419 [1956]). This mode of operation involves a method suitable only for the preparation of small amounts (up to 1 kg) of neohexanol in a laboratory. As for this reaction, another reducing method using sodium and ethanol (Sutter, Helv. 21: 1259 [1938]) is likewise unsuitable for industrial application on account of the high costs for the starting material.

All of the conventional processes, therefore, produce only low yields, require expensive technical apparatus, result in an unclean product, or utilize chemicals which are expensive and, due to the way they must be handled, are suitable only for laboratory work.

Thus, there is still great interest in finding a process enabling the production of a very pure neohexanol with a content of above 99.0%, in high yield with minor technical expenditure.

SUMMARY OF THE INVENTION

Accordingly, it is an object of this invention to provide such a process which overcomes or ameliorates the foregoing disadvantages.

It is another object of this invention to provide such a process involving the catalytic hydrogenation of dimethylbutyric acid or the ester thereof and wherein the purity of the neohexanol with respect to chlorine and sulfur contents permits subsequent catalytic dehydrogenation to neohexanal.

Upon further study for the specification and appended claims, further objects and disadvantages of this invention will become apparent to those skilled in the art. These objects have been attained by providing a process for the production of neohexanol with a purity of above 99%, a chlorine content of less than 10 ppm, and a sulfur content of less than 5 ppm, comprising esterifying 3,3-dimethylbutyric acid having a chlorine content below about 650 ppm with an alcohol of a normal boiling point above 117° C., optionally after distillatory separation into a portion richer in chlorine, with chlorine contents of above about 650 ppm, and a portion low in chlorine, with chlorine contents of below about 650 ppm, the chlorine content of the distillate being continuously controlled by sampling;

separating the ester, e.g., by distillation into fractions richer in chlorine with chlorine contents of above about 10 ppm and into fractions low in chlorine of below about 10 ppm, during which step the chlorine content of the distillate and/or the sump is continuously controlled by sampling; hydrogenating the ester low in chlorine with chlorine contents of below about 10 ppm to form neohexanol over a barium-activated copper chromite catalyst under a hydrogen pressure of 200–300 bar, at temperatures of 120°–220° C., and with catalyst loads of 0.05–1.0 liter of hydrogenation feed/liter of catalyst.-hour; and working up the hydrogenation product, e.g., by distillation, in a manner known per se.

DETAILED DISCUSSION

Surprisingly, neohexanol is obtained with a purity, as determined by gas chromatography, for example, of above 99.0% and in good yields by esterifying 3,3-dimethylbutyric acid with a chlorine content of below 650 ppm, preferably below 300 ppm, most preferably below 100 ppm (sulfur content, for example, 0.5 ppm), with an alcohol boiling above 117° C.; subjecting the ester to fractional distillation; combining the fractions, the chlorine content of which is <10 ppm; and hydrogenating this ester, low in chlorine, in the usual way over a copper chromite catalyst. From the resultant neohexanol, neohexanal can be obtained by catalytic dehydrogenation in surprisingly high yields.

These results are novel and surprising. With the large number of chlorine-containing impurities produced by reactions and polymerizations of the starting compounds used in and during the acid synthesis, it could not be foreseen that products with such low chlorine contents can be obtained by distillatory purification of the ester, optionally in combination with the distillatory purification of 3,3-dimethylbutyric acid. Surprisingly, a gap has been found in the broad spectrum of impurities.

Additionally, it was surprising that the hydrogenation of the dimethylbutyric acid esters to neohexanol, and use of the latter for the dehydrogenation to neohexanal, can be accomplished with high yields. For example, it is known that extensive branching in the carbon chain of esters greatly hamper their hydrogenation. For this reason, drastic conditions, for example high temperatures and long residence times, must be used for these compounds, and losses in yield must be tolerated due to decomposition. One example is the neopentyl glycol ester of monoisobutyric acid, whose hydrogenation is successful only under severe conditions (East German Patent No. 144,405 = U.S. Pat. No. 4,250,337, "Process for the Production of Pure Neopentyl Glycol").

It is furthermore known that neopentane is obtained from neohexanol under hydrogenation conditions, for example under a hydrogen pressure of 100 atmospheres, at 210°–225° C. and with Raney nickel as the catalyst (Ipatieff et al., Journal of American Chemical Society 73: 553 [1951]). Hydrogenation tests with the copper chromite catalyst, more suitable as compared with Raney nickel, wherein attempts were made as usual to obtain high conversion rates of more than 99%, confirmed the expectations: low-boiling compounds and water were found in the hydrogenation product. Only similar results could be expected for the hydrogenation of this invention.

The starting compound for the process of this invention is 3,3-dimethylbutyric acid, generally conventionally prepared from tert-butyl chloride or tert-butanol and vinylidene chloride. (See, for example, K Bott and H. Hellmann, "Angewandte Chemie" [Applied Chemistry]78: 932–936 [1966], which disclosure is incorporated of reference herein.) This starting compound contains, in part even after having been worked up, a number of chlorine compounds causing a chlorine content of, for example, 100–650 ppm, depending on the effort expended for distillatory purification. However, a chlorine content of above 10 ppm in the starting compound is not permissable for the catalytic hydrogenation of this invention. Otherwise, corrosion occurs in the highpressure hydrogenation reactor. Moreover, the hydrogenating catalyst rapidly loses its activity. Therefore, normal, commercially available 3,3-dimethylbutyric acid, even after having been purified by distillation, is unsuitable per se for the catalytic hydrogenation of this invention. As a result, the multi-step method of this invention has been provided.

Step (1): 3,3-Dimethylbutyric acid (DMBA), generally produced from tert-butyl chloride or tert-butanol and vinylidene chloride, can, optionally, first be subjected to fractional distillation. In this event, the chlorine content of the distillate is continuously controlled via conventional sampling procedures. The chlorine determination is made preferably by the Wickbold-combustion-method, in which the final determination is made photometrically (DIN 53474). Fractions having chlorine contents above 650 ppm, preferably above 100 ppm, are returned to the synthesis steps. All fractions having a lower chlorine content are combined (see, in this connection, Example 1.1) and processed further. Surprisingly, in spite of a practically constant boiling range of the fractions, fractionation takes place into fractions richer in chlorine and fractions poorer in chlorine as a function of time from beginning of distillation. Since the fractions poorer in chlorine still contain more than 10 ppm of chlorine, the thus-obtained DMBA is still unsuitable per se for the catalytic hydrogenation to neohexanol.

Step (2): DMBA with chlorine contents of below 650 ppm, preferably below 100 ppm, is esterified in the usual way with an alcohol (e.g. alkanol) boiling at a temperature above 117° C. (e.g., up to 260° C., 3 mbar) for example with n-butanol, n-pentanol, an isopentanol, n-hexanol, an isohexanol, n-heptanol, an isoheptanol, n-octanol, 2-ethyl-1-hexanol, or other isooctanol, etc., e.g., typically a $C_4$–$C_{20}$-alkanol. Especially suitable are the octanols, particularly n-octanol and 2-ethyl-1-hexanol. The esterification is fully conventional and carried out as disclosed, e.g., in Kirk Othmer Encyclopedia of Chemical Technology, 2. Ed. Vol. 8, page 313 and following pages. Interscience Publishers which disclosure is incorporated by reference herein. Alcohols with 1–3 C-atoms and isomeres of the n-butanol, that are alcohols with a boiling point lower than the boiling point of n-butanol (117,8° C.), are insuitable for this process. The examples 1.2.1, 1.2.2 and 1.2.3 demontrate that also with n-butanol the yields of low-chlorine esters are lower than with the octanols.

The resultant esters are fractionally distilled, the chlorine content of the distillate and/or of the sump being continuously controlled with the aid of sampling. Fractions having chlorine contents of $\leq 10$ ppm are combined (sulfur contents for example are 0.5–2 ppm; see in this connection Examples 1.2.1 through 1.2.4). Especially high yields of fractions low in chlorine are obtained with the octyl esters. For the butyl esters, the yields of low-chlorine fractions are lower. Surprisingly, a fractionation of the ester product into fractions richer in chlorine and fractions very low in chlorine content with <10 ppm of chlorine is possible for these esters, despite the practically identical boiling ranges included.

Step (3): The DMBA esters low in chlorine are hydrogenated under a hydrogen pressure of 200–300 bar and at temperatures of 120°–220° C., preferably 160°–180° C., over a barium-activated copper chromite catalyst. Preferably, the hydrogenation is continued up to a conversion of 80–99.0%, most preferably up to 97.0%. The conversion rate is set using conventional considerations of the activity condition of the catalyst as a function of the temperature and the load on the reactor. Loads of 0.05–1.0 liter, preferably of 0.1–0.5 liter of hydrogenation feed/liter of catalyst/hour are usually employed.

The above-mentioned barium-activated copper chromite catalysts are per se conventional as are their use unless indicated otherwise herein (see, e.g., U.S. Pat. Nos. 2,137,407; 2,091,800; 2,782,243; and 2,544,711, as well as Adkins et al., Journal of American Chemical Society 53: 1091 [1931]; Journal of American Chemical Society 53: 1095 [1931]; Journal of American Chemical Society 54: 1145 [1932]; Connor et al, Journal of American Chemical Society 54: 1138 [1932]; Adkins et al, Journal of American Chemical Society 72: 2626 [1950], all of whose disclosures are incorporated of reference herein), and have the following composition, for example: 35% CuO, 38% $CrO_3$, 10% BaO, as well as $SiO_2$ as the binder. The catalyst can be conventionally applied to a support.

All reaction components used in the esterification and hydrogenation etc., must also be essentially chlorine and sulfur-free as described herein, e.g., must meet the chlorine and sulfur purities specified herein for DMBA and its derivatives at various stages of the process.

The hydrogenation products discharged from the reactor are worked up by distillation, yielding neohexanol with a purity as determined, for example, by gas chromatography of more than 99.0%; in most cases (see examples), the purity is at 99.9%

Because of its high purity, the neohexanol prepared according to this invention is suitable for catalytic dehydrogenation. The chlorine and sulfur contents are below 10 and 5 ppm, respectively, in general 1-4 ppm of chlorine and 0.5-1 ppm of sulfur.

The dehydrogenation to neohexanal can likewise be effected with barium-activated copper chromite catalysts; it is possible to use the same catalysts employed for the ester hydrogenation. This reaction is carried out fully conventionally, e.g., as disclosed in Kirk Othmer, Encyclopedia of Chemical Technology, 2. Ed., Vol. 1, page 646 (1963); Interscience Publishers, which disclosure is incorporated of reference herein.

The neohexanol obtained according to the process of this invention, and the neohexanal prepared therefrom, are valuable intermediates for numerous further technical syntheses, e.g., for the syntheses of phthalic acid esters as plasticisers for PVC (British Pat. No. 693,390) and of odoriferous substances, and, as well, as solvents in the many applications of alcoholic aldehyde and solvents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

1.1

Distillatory separation of 3,3-dimethylbutyric acid (DMBA) into fractions with chlorine contents of above 650 ppm and into fractions with chlorine contents of below 650 ppm, preferably below 100 ppm.

1.1.1

Under the conditions indicated in the table, 2,476 g of a DMBA with a purity (according to GC analysis) of 99.99%, a chlorine content of 110 ppm, a sulfur content of 0.5 ppm, an acid number of 488.7 (theoretical acid number=483.6), and an ester number of 2.3 is distilled on a heated glass column having a length of 0.5 m and filled with multifill packing. The chlorine content of the distillate is checked continuously with the aid of samples.

| Fr. No. | Boiling Range °C. | Weight g | Weight % | Pressure mbar | Ratio Reflux: Prod. | Chlorine Content ppm |
|---|---|---|---|---|---|---|
| 1 | 80-81 | 49 | 2.0 | 13 | 10:1 5:1 | 3300 |
| 2 | 80-81 | 45 | 1.8 | 13 | 5:1 | n.d.(*) |
| 3 | 80-81 | 47 | 1.9 | 13 | 5:1 | 320 |
| 4 | 80-81 | 60 | 2.4 | 13 | 5:1 | n.d. |
| 5 | 80-81 | 70 | 2.8 | 13 | 5:1 | 180 |
| 6 | 80-81 | 439 | 17.8 | 13 | 5:1 | 85 |
| 7 | 80-81 | 318 | 12.8 | 13 | 5:1 | 68 |
| 8 | 80-81 | 314 | 12.7 | 13 | 5:1 | 36 |
| 9 | 80-81 | 412 | 16.6 | 13 | 5:1 | 24 |
| 10 | 80-81 | 322 | 13.0 | 13 | 5:1 | 18 |
| 11 | 80-81 | 382 | 15.4 | 13 | 5:1 | 14 |
| Residue | | 16 | 0.6 | | | |
| Cooling Trap | | 2 | 0.1 | | | |
| Total | | 2476 | 99.9 | | | |

(*)n.d. = not determined

As per the chlorine contents (last column of the table), the fractions 3-11 with chlorine contents of below 650 ppm and especially fractions 6-11 with chlorine contents of below 100 ppm are suitable for the subsequent esterification, just as the starting compound with 110 ppm of chlorine.

1.1.2.

912 g of a DMBA with a purity (according to GC analysis) of 98.5%, a chlorine content of 610 ppm, a sulfur content of 4 ppm, an acid number of 479.2 (theoretical acid number=483.6), and an ester number of 2.3 is distilled under the conditions indicated in the table below on a heated glass column having a length of 0.5 m and filled with 4×4 mm glass Raschig rings. The chlorine content of the distillate is continuously controlled by sampling.

| Fr. No. | Boiling Range °C. | Weight g | Weight % | Pressure mbar | Ratio Reflux: Prod. | Chlorine Content ppm |
|---|---|---|---|---|---|---|
| 1 | 78 | 93 | 10.6 | 13 | 5:1 | 1300 |
| 2 | 78 | 91 | 10.3 | 13 | 5:1 | 530 |
| 3 | 78 | 88 | 10.0 | 13 | 5:1 | 370 |
| 4 | 78 | 90 | 10.2 | 13 | 5:1 | 260 |
| 5 | 78 | 94 | 10.7 | 13 | 5:1 | 170 |
| 6 | 78 | 88 | 10.0 | 13 | 5:1 | 105 |
| 7 | 78-79 | 91 | 10.3 | 13 | 5:1 | 73 |
| 8 | 78-79 | 91 | 10.3 | 13 | 5:1 | 54 |
| 9 | 78-79 | 92 | 10.5 | 13 | 5:1 | 24 |
| 10 | 78-79 | 58 | 6.7 | 13 | 5:1 | 28 |
| Residue | | 3 | 0.3 | | | |
| Total | | 879 | 99.9 | | | |

In accordance with the chlorine contents, suitable for the subsequent esterification are, besides the feed material with 610 ppm chlorine, preferably fractions 2-10 with chlorine contents of below 650 ppm and especially fractions 7-10 with chlorine contents of below 100 ppm.

1.2 Esterification of DMBA

1.2.1 Butyl Ester of DMBA 12 moles of DMBA having a chlorine content of 110 ppm (feed product of Example 1.1.1) is esterified as usual at temperatures of 136°-190° C. (start of esterification at 136° C., ending at 190° C. sump temperature) with 12 moles of n-butanol and 4.18 g (=0.3% by weight, based on DMBA) of butyl titanate, the thus-formed water being discharged from the cycle together with the n-butanol. The resultant butyl ester (2,275 g) is then distilled on a heated glass column having a length of 0.5 m and being filled with multifil packing.

| Fr. No. | Boiling Range °C. | Weight g | Weight % | Pressure mbar | Ratio Reflux:Prod. | Chlorine Content ppm |
|---|---|---|---|---|---|---|
| 1 | 93–178 | 325 | 14.3 | N(**) | 3:1 | n.d.(*) |
| 2 | 61–69 | 29 | 1.3 | 13 | 10:1 | 460 |
| 3 | 69 | 91 | 4.0 | 13 | 10:1 | 165 |
| 4 | 69 | 50 | 2.2 | 13 | 10:1 | 100 |
| 5 | 70 | 76 | 3.3 | 13 | 10:1 | 170 |
| 6 | 70 | 67 | 2.9 | 13 | 10:1 | n.d. |
| 7 | 70 | 51 | 2.2 | 13 | 10:1 | 48 |
| 8 | 70 | 65 | 2.9 | 13 | 10:1 | n.d. |
| 9 | 70 | 62 | 2.7 | 13 | 10:1 | 70 |
| 10+ 11 | 70 | 153 | 6.7 | 13 | 10:1 | n.d. |
| 12 | 70 | 66 | 2.9 | 13 | 10:1 | 3 |
| 13– 15 | 70 | 209 | 9.2 | 13 | 10:1 | n.d. |
| 16 | 70 | 91 | 4.0 | 13 | 10:1 | 2 |
| 17– 19 | 70 | 264 | 11.6 | 13 | 10:1 | n.d. |
| 20 | 71 | 75 | 3.3 | 13 | 10:1 | 1 |
| 21– 25 | 71 | 393 | 17.3 | 13 | 10:1 | n.d. |
| 26 | 71 | 71 | 3.1 | 13 | 10:1 | 5 |
| 27 | 71 | 51 | 2.2 | 13 | 10:1 | 5 |
| 28+ 29 | 71–73 | 56 | 2.5 | 13 | 10:1 | 120 |
| Residue | | 28 | 1.2 | | | |
| Cooling Trap | | 2 | 0.1 | | | |
| Total | | 2275 | 99.9 | | | |

(*)n.d. = not determined
(**)N = normal pressure

Fractions 12–27 with chlorine contents of below 10 ppm and sulfur contents of 2 ppm are suitable for the subsequent catalytic hydrogenation. The quantity of fractions 12 through 27 amounts to 1,220 g=53.6% of the feed.

1.2.2. n-Octyl Ester of DMBA 1,160 g (=10 moles) of DMBA with a chlorine content of 110 ppm (fractions 4–10 of 1.1.2) is esterified with 1,560 g (=12 moles) of n-octanol in the presence of 3.35 g (=0.3% by weight) of butyl titanate, based on DMBA. The sump temperature rises within 2 hours from 168° to 234° C. and remains for 3 hours at this temperature. The thus-formed water is removed from circulation with the aid of the excess n-octanol. Esterification is completed after a total of 5 hours. The acid number is 0.8.

The thus-obtained raw ester, 2,505 g, is distilled on a heated glass column having a length of 0.5 m and filled with multifil packing.

| Fr. No. | Boiling Range °C. | Weight g | Weight % | Pressure mbar | Ratio Reflux:Prod. | Chlorine Content ppm |
|---|---|---|---|---|---|---|
| 1 | 85–127 | 266 | 10.6 | 13 | 3:1 20:1 | 47 |
| 2 | 127–128 | 2196 | 87.9 | 13 | 20:1 3:1 | 8 |
| Residue | | 35 | 1.4 | | | |
| Cooling Trap | | 2 | 0.1 | | | |
| Total | | 2499 | 100.0 | | | |

Fraction 2 has the desired, low chlorine content of <10 ppm; the purity (according to GC analysis) is 99.8%. The n-octyl ester of this purity is obtained in a yield of 97.2%, based on DMBA employed. The sulfur content is 0.5 ppm.

1.2.3 2-Ethylhexyl Ester of DMBA 1,044 g (=9 moles) of DMBA having a chlorine content of 80 ppm (fractions 5–10 of Example 1.1.2) is esterified with 1,300 g (=10 moles) of 2-ethyl-1-hexanol with a chlorine content of 0.5 ppm in the presence of 3.13 g of butyl titanate at temperatures of 167°–244° C. (start of esterification at 167° C., ending at 244° C. sump temperature) in correspondence with the description of Example 1.2.2. After 4.5 hours, the esterification is completed. The acid number is 0.2. The thus-obtained raw ester, 2,119 g, is distilled on a heated glass column having a length of 0.5 m and filled with 4×4 mm glass Raschig rings.

| Fr. No. | Boiling Range °C. | Weight g | Weight % | Pressure mbar | Ratio Reflux:Prod. | Chlorine Content ppm |
|---|---|---|---|---|---|---|
| 1 | 85–89 | 94 | 4.5 | 13 | 5:1 | 400 |
| 2 | 89–124 | 159 | 7.6 | 13 | 20:1 | 275 |
| 3 | 124 127 | 1813 | 87.1 | 13 16 | 20:1 1:1 | 3(*) |
| Residue | | 16 | 0.8 | | | |
| Total | | 2082 | 100.0 | | | |

(*)The chlorine content was determined in a sump sample after removing fractions 1 and 2 by distillation.

The purity of the ester, fraction 3 (according to GC analysis), is 99.9%, the yield of ester with low chlorine content is 88.4%.

1.2.4 2-Ethylhexyl Ester of DMBA

DMBA is esterified with 2-ethyl-1-hexanol according to the data provided in Example 1.2.3, but instead of using a DMBA with 85 ppm of chlorine, a DMBA is employed with a chlorine content of 610 ppm (starting compound of Example 1.1.2). Yield: 1,855 g of a raw ester which is distilled as in Example 1.2.3 on a heated glass column having a length of 0.5 m and filled with glass Raschig rings (4×4 mm).

| Fr. No. | Boiling Range °C. | Weight g | Weight % | Pressure mbar | Ratio Reflux:Prod. | Chlorine Content ppm A: in Distillate B: in Sump |
|---|---|---|---|---|---|---|
| 1 | 95 94–95 | 96 | 6.5 | 30 26 | 20:1 | A: 720 B: 120 |
| 2 | 97–131 | 98 | 6.7 | 20–22 | 20:1 | A: 675 B: 85 |
| 3 | 129–131 | 163 | 11.1 | 22 | 20:1 | A: 33 B: 82 |
| 4 | 131 | 174 | 11.8 | 21 | 20:1 | A: 17 B: 105 |
| 5 | 130 | 152 | 10.3 | 22 | 20:1 | A: 15 B: 95 |
| 6 | 130–131 | 264 | 18.0 | 20–22 | A: 13 | B: 140 |
| 7 | 130 | 260 | 17.7 | 18–20 | 20:1 | A: 8 B: 210 |
| 8 | 130 | 152 | 10.3 | 20 | 20:1 | A: 23 B: n.d. |
| Residue | | 100 | 6.8 | | | |
| Cooling Trap | | 11 | 0.7 | | 308 g was used up for analyses | |
| Total | | 1470 | 99.9 | | | |

After each fraction, a 20 gram sample was taken of the distillate and of the sump product, and the chlorine content determined, as listed in the last column of the table under (A) and (B), respectively. These values demonstrate that the desired chlorine concentration of <10 ppm was attained only by fraction 7.

Thus, the effectiveness of this mode of operation to obtain esters low in chlorine is lessened in case of chlorine contents of the DMBA feed of 610 ppm.

1.3 Catalytic Hydrogenation of the DMBA Ester to Neohexanol

1.3.1 Hydrogenation of the DMBA n-Octyl Ester

The hydrogenation of the DMBA n-octyl ester, fraction 2 of Example 1.2.2, takes place at 190° C. and under a hydrogen pressure of 300 bar over a barium-activated copper chromite catalyst of the composition: approximately 33% CuO, about 38% $CrO_3$, about 10% BaO, remainder $SiO_2$ (1300 ml).

The reactor employed is a 1.5-liter high-pressure reactor; 100 ml/h of ester is continuously introduced in metered amounts. The load on the catalyst bed is 0.077 liter of ester/liter of catalyst.hour.

The hydrogenation product has a water content of 2.9%, an acid number of 0.04, and a saponification number of 0.7. The ester conversion is 99.7%. In a test distillation, C-7 and C-8 hydrocarbons are obtained as forerunnings due to decomposition of the alcohols. The neohexanol yield is about 83%, and the n-octanol yield is 65%, based on the feed. The distilled neohexanol, according to GC analysis, has a purity of 99.7%, a chlorine content of 2 ppm, and a sulfur content of 0.5 ppm.

1.3.2 Hydrogenation of DMBA 2-Ethylhexyl Ester at Lower Conversion Rate

In a hydrogenating furnace, capacity 450 ml (filled with 400 ml of catalyst), 100 ml/h of the DMBA 2-ethylhexyl ester (purity according to GC analysis 99.9%, chlorine content 2.5 ppm, sulfur content 0.5 ppm, acid number 0.2, saponification number 116, water content 0.11%) is hydrogenated at 170° C. and under a pressure of 300 bar over the catalyst described in Example 1.3.1 with a conversion of 92.1%. The catalyst load is 0.25 liter of ester/liter of catalyst.hour. The unreacted ester is separated from the thus-formed alcohols by distillation. A sample run of the hydrogenation product shows the following characteristic data:

| Acid Number | 0.1 | Water Content | 0.8 |
|---|---|---|---|
| CO Number | 0.68 | Chlorine Content | 2 ppm |
| Bromine Number | 0.37 | Sulfur Content | 0.5 ppm |
| Saponification Number | 6.4 | | |

The hydrogenated product, 906 g, is distilled on a heated glass column having a length of 0.5 m and filled with multifil packing.

| Fr. No. | Boiling Range °C. | Weight g | Pressure N = normal mbar | Ratio Reflux: Prod. | Main Product |
|---|---|---|---|---|---|
| 1 | 66–145 | 6 | N | 5:1 | Forerun |
| 2 | 145 | 354 | N | 5:1 | Neo- |
|   | 91–93 |   | 133 | 3:1 | hexanol |
| 3 | 93–124 | 12 | 133 | 3:1 | Intermediate Run |
|   |   |   |   | 5:1 |  |
| 4 | 124–125 | 448 | 133 | 3:1 | 2-Ethyl- |
| 5 | 125–176 | 65 | 133 | 3:1 | 1-hexanol Ester |
| Residue | 16 | | | | |
| Cooling Trap | 4 | | | | |
| Total | 905 | | | | |

The cooling trap product is added to fraction 1. This mixture contains, according to GC analysis, 96.8% neohexanol. Hydrocarbons are formed only in traces.

Fraction 2 is neohexanol with a purity of 99.9%, a chlorine content of 1 ppm, and a sulfur content of 0.5 ppm.

Then comes an intermediate run consisting of 22.0% of neohexanol and 76.3% of 2-ethylhexanol. Fraction 4 is 2-ethylhexanol with a 99.9% purity. Fraction 5 contains, besides 8.1% of 2-ethyl-1-hexanol, 88.7% of ester which was not hydrogenated.

The residue contains 87.3% of ester besides several high-boiling components.

From these numerical data, a conversion rate during hydrogenation is calculated amounting to 92.1%. The yields in neohexanol and 2-ethyl-1-hexanol both are 98.6%, based on the conversion.

Consequently, by the somewhat lower conversion rate, the yield in neohexanol has been considerably increased, and the purity of the neohexanol has not been impaired.

1.3.3

The hydrogenation is conducted according to the description of Example 1.3.2, but at a temperature of 160° C.

A test run of the hydrogenation product shows a saponification number of 6.3 and a water content of 0.16%. The test distillation takes place according to the data provided in Example 1.3.2 and leads to the following result:

| Conversion: | 83.2% |
|---|---|
| Yields (Based on Conversion): | Neohexanol and 2-Ethylhexanol 99.1% |
| Purity of Neohexanol: | 99.9% |
| Chlorine Content: | 1 ppm |
| Sulfur Content: | 0.5 ppm |

1.3.4

The hydrogenation is performed according to the disclosure in Example 1.3.2, but at a temperature of 180° C. With a conversion rate of 96.5%, yields of neohexanol and 2-ethylhexanol are obtained of 98.0%. The purity of the neohexanol is 99.8%, the chlorine content is 1 ppm, and the sulfur content is 0.5 ppm.

1.3.5 Hydrogenation of DMBA n-Hexyl Ester

The DMBA n-hexyl ester (purity 99.6%, chlorine content 9 ppm, sulfur content 1.5 ppm) is hydrogenated analogously to Example 1.3.2 at a temperature of 170° C. up to a conversion of 93.5%. The neohexanol and n-hexanol yields are 97.8%. The purity of the distilled neohexanol is 99.7%. The chlorine content is 4 ppm, the sulfur content 1 ppm.

1.3.6 Hydrogenation of DMBA n-Butyl Ester

The hydrogenation of the DMBA n-butyl ester (purity 99.5%, chlorine content 4 ppm, sulfur content 1 ppm, fractions 12-27 of Example 1.2.1) is performed according to the data provided in Example 1.3.2 at a temperature of 165° C. up to a conversion rate of 90.5%.

The resultant neohexanol has a purity of 99.1%, a chlorine content of 2 ppm, and a sulfur content of 0.5 ppm.

1.3.7 Hydrogenation of DMBA Neohexyl Ester

The DMBA neohexyl ester (boiling range, under a pressure of 133 mbar, 135°-137° C., purity 99.2%, chlorine content 7 ppm, sulfur content 1 ppm) is hydrogenated according to the description in Example 1.3.2 at 160° C. up to a conversion of 85%. The neohexanol is obtained in a purity of 99.2%, with a chlorine content of 3 ppm and a sulfur content of 0.5 ppm.

1.4 Use of the Pure Neohexanol Prepared According to This Invention for the Catalytic Dehydrogenation to Neohexanal 1.4.1 The reactor utilized is an electrically heated glass tube having a diameter of 50 mm and a length of 700 mm, equipped with three temperature measuring sites (bottom, middle, and head of the reactor). Per hour, 216 g of neohexanol (purity 99.9%, chlorine content 1 ppm, sulfur content 0.5 ppm, of Example 1.3.2) is pumped into a vaporizer, and 56 l/h of nitrogen is passed through the vaporizer. The evaporated neohexanol and the nitrogen are introduced at the head of the reactor. The reactor contains the catalyst, 1,300 ml or g of the barium-activated copper chromite catalyst described in Example 1.3.1. The catalytic dehydrogenation is conducted at the following temperatures in the reactor:

| | |
|---|---|
| Head of reactor | 220° C. |
| Middle of reactor | 180° C. |
| Bottom of reactor | 240° C. |

The dehydrogenation product is worked up by distillation. A neohexanal yield of 93.5% is obtained, based on reacted neohexanol, with a conversion rate of 28.8%. The purity of the neohexanal is 99.3%.

1.4.2

Pure neohexanol is dehydrogenated according to the description of Example 1.4.1, but at a temperature at the head of the reactor of 235° C., in the center of the reactor of 195° C., and at the bottom of the reactor of 255° C. A neohexanal yield is obtained, based on reacted neohexanol, of 87.1% with a conversion of 51.5%. The resultant neohexanal has a purity of 99.1%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of neohexanol of a purity of above 99%, a chlorine content of less than 10 ppm, and a sulfur content of less than 5 ppm, comprising
   esterifying 3,3-dimethylbutyric acid of a chlorine content below 650 ppm with an alkanol of a normal boiling point above 117° C.;
   separating the ester by distillation into chlorine rich fractions of chlorine contents above 10 ppm and chlorine poor fractions of chlorine contents below 10 ppm, during which step the chlorine content of the distillate or the sump is continuously controlled by sampling;
   hydrogenating the ester with a chlorine content below 10 ppm to form neohexanol, over a barium-activated copper chromite catalyst under a hydrogen pressure of 200-300 bar, at a temperature of 120°-220° C., and with a catalyst load of 0.05-1.0 liter of hydrogenation feed/liter of catalyst.hour.

2. A process of claim 1 further comprising, prior to the esterification step, separating the 3,3-dimethylbutyric acid by distillation into a chlorine rich fraction of a chlorine content above 650 ppm and a chlorine poor fraction of a chlorine content below 650 ppm, during which step the chlorine content of the distillate is continuously controlled by sampling.

3. A process of claim 1 further comprising, prior to the esterification step, separating the 3,3-dimethylbutyric acid by distillation into a chlorine rich fraction of a chlorine content above 100 ppm and a chlorine poor fraction of a chlorine content below 100 ppm, during which step the chlorine content of the distillate is continuously controlled by sampling, and then only the latter chlorine poor fraction is passed onto the subsequent esterification step.

4. A process of claim 1 or 3, wherein the alkanol is an octyl alcohol.

5. A process of claim 1 or 3 wherein the alkanol is n-octanol or 2-ethyl-1-hexanol.

6. A process of claim 1 or 2 wherein the hydrogenation is carried out up to a conversion of 80-99%.

7. A process of claim 4 wherein the hydrogenation is carried out up to a conversion of 80-99%.

8. A process of claim 5 wherein the hydrogenation is carried out up to a conversion of 80-99%.

9. A process of claim 6 wherein said conversion is 80-97%.

10. A process of claim 4 wherein the hydrogenation is carried out up to a conversion of 80-97%.

11. A process of claim 5 wherein the hydrogenation is carried out up to a conversion of 80-97%.

12. A process of claim 1 or 2 wherein the alkanol is n-butanol, n-pentanol, an isopentanol, n-hexanol, an isohexanol, n-heptanol, an isoheptanol, n-octanol, 2-ethyl-1-hexanol, or other isooctanol.

13. A process of claim 1 or 2 wherein the hydrogenation temperature is 160°-180° C.

14. A process for the preparation of neohexanol comprising,
   preparing neohexanol of a purity above 99%, a chlorine content <10 ppm and a sulfur content <5 ppm by a process comprising
   esterifying 3,3-dimethylbutyric acid of a chlorine content below 650 ppm with an alkanol of a normal boiling point above 117° C.;
   separating the ester by distillation into chlorine rich fractions of chlorine contents above 10 ppm and chlorine poor fractions of chlorine contents below 10 ppm, during which step the chlorine content of the distillate or the sump is continuously controlled by sampling;

hydrogenating the ester with a chlorine content below 10 ppm to form neohexanol, over a barium-activated copper chromite catalyst under a hydrogen pressure of 200-300 bar, at a temperature of 120°-220° C., and with a catalyst load of 0.05-1.0 liter of hydrogenation feed/liter of catalyst.hour; and dehydrogenating the resultant neohexanol to form neohexanal.

* * * * *